(12) United States Patent
Yim et al.

(10) Patent No.: US 7,521,188 B2
(45) Date of Patent: Apr. 21, 2009

(54) OPTICAL MONITORING OF CLEAVING ENZYME ACTIVITY

(75) Inventors: Hyoungsik Yim, Ann Arbor, MI (US); Mark E. Meyerhoff, Ann Arbor, MI (US); Youngmi Lee, Knoxville, TN (US)

(73) Assignee: The Regents of The University of Michigan, Ann Arbor, MI (US)

( * ) Notice: Subject to any disclaimer, the term of this patent is extended or adjusted under 35 U.S.C. 154(b) by 386 days.

(21) Appl. No.: 11/070,568

(22) Filed: Mar. 2, 2005

(65) Prior Publication Data

US 2006/0199186 A1 Sep. 7, 2006

(51) Int. Cl.
  *C12Q 1/68* (2006.01)
  *C07H 21/04* (2006.01)
  *C07K 14/47* (2006.01)
(52) U.S. Cl. .......................... 435/6; 530/350; 536/23.2; 435/23

(58) Field of Classification Search ....................... None
See application file for complete search history.

(56) References Cited

U.S. PATENT DOCUMENTS

| 5,487,972 | A * | 1/1996 | Gelfand et al. ................. 435/6 |
| 6,692,917 | B2 * | 2/2004 | Neri et al. ...................... 435/6 |
| 6,703,205 | B2 | 3/2004 | Kopf-Sill et al. |
| 6,913,881 | B1 | 7/2005 | Aizenstein et al. |
| 2002/0197649 | A1 * | 12/2002 | Singh ......................... 435/7.1 |
| 2006/0199187 | A1 * | 9/2006 | Meyerhoff et al. ............. 435/6 |

* cited by examiner

*Primary Examiner*—Anand U Desai
(74) *Attorney, Agent, or Firm*—Dierker & Associates, P.C.

(57) ABSTRACT

A marker molecule for monitoring cleaving enzyme activity is disclosed. The marker molecule includes a protein, a peptide, or an oligonucleotide. A co-factor is conjugated to the protein, the peptide, or the oligonucleotide, thereby forming a co-factor labeled protein, a co-factor labeled peptide, or a co-factor labeled oligonucleotide. The co-factor is adapted to produce an enzymatic signal that is optically detectable.

7 Claims, 5 Drawing Sheets

US 7,521,188 B2

SEQUENCE LISTING

<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: Synthetic
Probe for P.pachyrhizi

<400> SEQUENCE: 1
ccaaaaggta cacctgtttg agtca 25

OPTICAL MONITORING OF CLEAVING ENZYME ACTIVITY

BACKGROUND

The present disclosure relates generally to optically monitoring of cleaving enzyme activity, and more particularly to the optical detection of enzyme (polymerase, DNase, and protease, etc.) activity using a specially designed co-factor labeled protein or oligonucleotide.

Genetic testing and enzyme-based assays have the potential for use in a variety of applications, ranging from genetic diagnostics of human diseases to detection of trace levels of pathogens in food products. Currently, more than 400 diseases can be diagnosed by molecular biology analysis of nucleic acid sequences. It is likely that additional tests will be developed as further genetic information becomes available. DNA diagnostic devices enable clinicians to efficiently detect the presence of a whole array of genetically based diseases, including, for example, AIDS, Alzheimer's, and various forms of cancer.

DNA amplification processes are currently used for real-time and end-point detection of specific DNA sequences. The current chemistries allow detection of PCR products via the generation of a fluorescent signal. Generally, the required reagents for these systems are expensive to synthesize, and in some instances, the systems require use of expensive fluorescence instrumentation for detection. Some techniques include binding dye to a double stranded DNA sequence and thus do not use a probe designed for any particular target being analyzed. However, detection of PCR amplified DNA by such a method requires extensive optimization since the dye cannot distinguish between specific and non-specific products accumulated during PCR. With this type of technique, follow-up assays are used, in some instances, to validate obtained results.

The rising use of DNA and/or protein diagnostic testing devices has produced a need for low-cost, highly portable DNA and/or detection devices (for example, a glucometer-type "lab-on-a-chip" device) for use in various markets including health care, agriculture, food testing and bio-defense. Generally, it would be desirable that any new DNA and/or protein diagnostic devices integrate several functional analysis components within the same platform. Further, it would be desirable that such devices be reliable, inexpensive, and able to simplify the monitoring of PCR (polymerase chain reaction) and EA (cleaving enzyme activity).

SUMMARY

A marker molecule for monitoring cleaving enzyme activity is disclosed. The marker molecule includes a protein, a peptide, or an oligonucleotide. A co-factor is conjugated to the protein, the peptide, or the oligonucleotide, thereby forming a co-factor labeled protein, a co-factor labeled peptide, or a co-factor labeled oligonucleotide. The co-factor is adapted to produce an enzymatic signal that is optically detectable.

A method of monitoring cleaving enzyme activity in a sample is also disclosed. The method includes exposing a co-factor labeled protein, peptide, or oligonucleotide to cleaving activity. The co-factor labeled protein, peptide, or oligonucleotide includes a protein, peptide, or oligonucleotide and a co-factor conjugated to the protein, peptide, or nucleotide. This exposure releases a fragment including the co-factor. The fragment is then combined with an apo-enzyme. Combining the fragment having the co-factor with the apo-enzyme produces an enzymatic signal that is optically detectable. The enzymatic signal, which is optically detectable, confers detection of cleaving activity.

BRIEF DESCRIPTION OF THE DRAWINGS

Objects, features and advantages of embodiments of the present invention will become apparent by reference to the following detailed description and drawings, in which.

DETAILED DESCRIPTION

Embodiment(s) disclosed herein advantageously combine a marker molecule (e.g. a co-factor labeled protein, peptide, or nucleotide) and the production of an enzyme amplified optically detectable signal, both of which may be incorporated into a DNA diagnostic device or an EA monitoring device. This combination provides an enzyme-based optical method to detect DNA amplified via polymerase chain reaction (PCR) or to monitor cleaving enzyme activity (EA). It is to be understood that embodiment(s) of the marker molecule may be integrated with, for example, a litmus paper-type strip sensing system for end-point PCR detection or EA in a flow-through system with a visible spectrometer.

Figure 1:
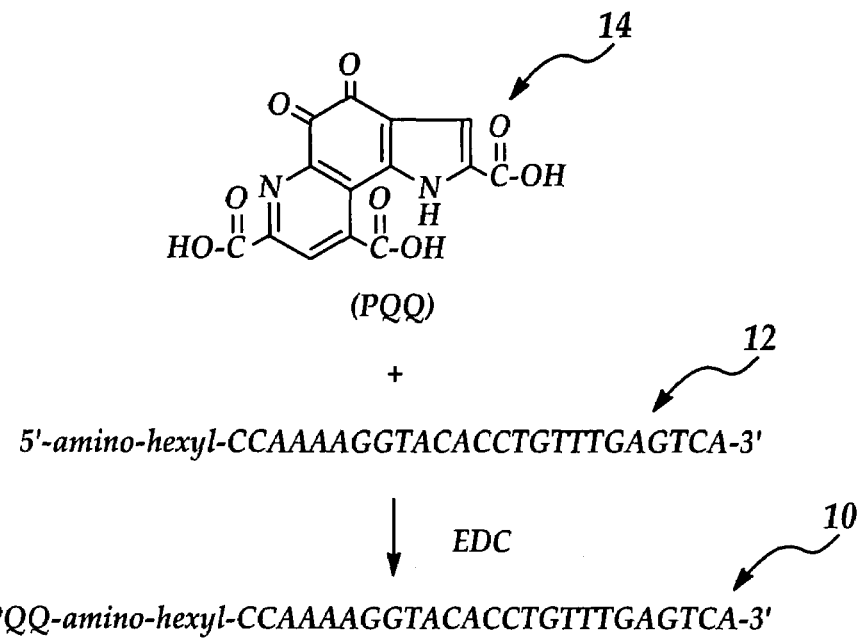
FIG. 1 is a schematic flow diagram illustrating an embodiment of making an embodiment of a prosthetic group (PQQ) labeled oligonucleotide.

Referring now to FIG. 1, an embodiment of making a labeled oligonucleotide 10 (i.e. marker molecule) is schematically depicted. Generally, embodiments of the labeled oligonucleotide 10 include a site-specific sequence 12 labeled with a co-factor (CF) 14. The co-factor (CF) 14 may be conjugated at any spot along the site-specific sequence 12. In non-limitative example embodiments, the co-factor (CF) 14 may be attached to the 5' end, the 3' end, and/or anywhere between the two ends.

In an alternate embodiment, the marker molecule 10 is a labeled peptide or a labeled protein. Generally, these embodiments include a co-factor conjugated to a selected protein or peptide.

In the non-limitative example shown in FIG. 1, the co-factor (CF) 14 (PQQ) is conjugated at the 5' end of the site-specific sequence 12 by adding 1-(3-dimethylaminopropyl)-3-ethylcarbodiimide (EDC or EDAC; 1 mg/ml) into a PQQ solution. After reaction of the PQQ with EDAC at about 4° C., N-hydroxysuccinimide (NHS; 0.6 mg/ml) is injected into the solution and shaken. This results in the modification of the carboxyl groups and the formation of amine-reactive NHS esters. A solution of the desired 5'amine-derivatized oligonucleotide may be added to the activated PQQ and allowed to react. In an example embodiment, the oligonucleotide solution contains a 5'amine and a carbon molecule (e.g. $(CH_2)_x$).

In embodiment(s) of the method, the co-factor (CF) 14 is adapted to produce an enzymatic signal that is optically detectable. As used herein, the term "produce" means indirectly or directly generating the enzymatic signal. In a non-limitative example, indirectly producing includes binding the co-factor (CF) 14 to an apo-enzyme to form an activated enzyme that is capable of catalyzing a reaction that results in an optically detectable enzymatic signal.

Generally, as described in more detail hereinbelow, the co-factor (CF) 14 portion of the marker molecule 10 binds with an apo-enzyme. Non-limitative examples of the co-factor (CF) 14 include prosthetic groups (organic and covalently bound to an enzyme), co-enzymes (organic and non-covalently bound to an enzyme), and metal-ion activators. Specific non-limitative examples of co-factors 14 include pyrroloquinoline quinine (PQQ), flavin adenine dinucleotide (FAD), nicotinamide adenine dinucleotide phosphate (NADP), heme, and the like. Non-limitative examples of metal ion activators include iron, copper, manganese, magnesium, zinc, and the like, and combinations thereof.

The non-limitative example shown in FIG. 1 depicts pyrroloquinoline quinone (PQQ) as the co-factor (CF) 14, and 5'-amino-hexyl-CCAAAAGGTACACCTGTTTGAGTCA-3' as the site-specific sequence 12. The PQQ is conjugated to the amino group of the sequence 12. The non-limitative example of marker molecule 10 shown in FIG. 1 is capable of detecting target DNA from P.pachyrhizi. It is to be understood, however, that the marker molecule 10 may be made complementary to any target DNA. Further, the marker molecule 10 may be designed to hybridize or anneal to its complementary single strand DNA sequence within an amplicon domain defined by a pair of primer oligonucleotides or between forward and reverse primers.

Figure 2:
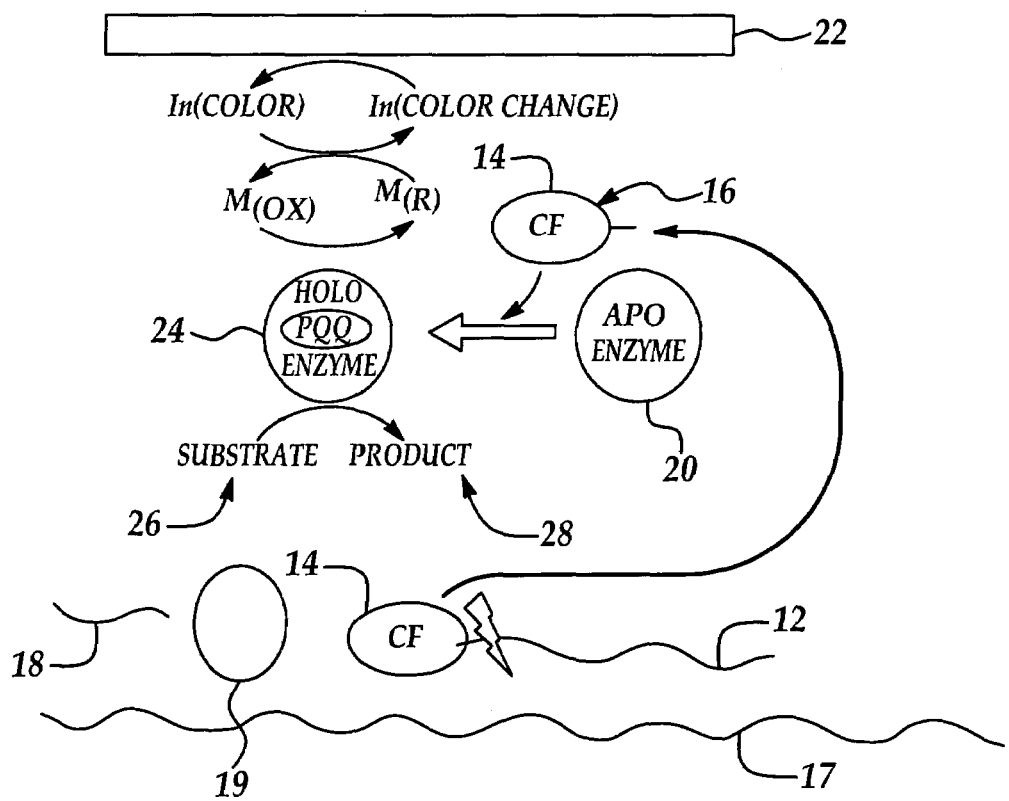
FIG. 2 is a schematic view of an embodiment of a method of detecting DNA.

Referring now to FIG. 2, an embodiment of the method of detecting target DNA in a sample using an embodiment of the labeled oligonucleotide 10 is schematically depicted. Embodiment(s) of the method integrate DNA amplification processes (non-limitative examples of which include real-time and end-point PCR) with enzymatic signal amplification. More specifically, PCR-dependent exonuclease activity can trigger enzymatic generation or amplification of a measurable optical enzymatic signal. The enzymatic signal(s) may be optically detectable via absorbance change, fluorescence, visual color change, electrochemistry, and combinations thereof.

Embodiment(s) of the method generally include performing a DNA amplification process on a sample 17, exposing an embodiment of the probe 10 to exonuclease activity, combining a co-factor (CF) 14 probe fragment 16 to an apo-enzyme 20, and optically detecting an enzymatic signal that results from the combination of the co-factor (CF) 14 with the apo-enzyme 20. It is to be understood that these steps may be performed substantially simultaneously or sequentially.

Non-limitative examples of the DNA amplification processes include end-point PCR, real-time PCR, and RCA. Either PCR process may include a PCR mixture and/or sample formulated such that it is compatible with desired chemistries for enzymatic signal amplification and optical detection. Such a formulation may include, but is not limited to the following: substrate(s) (a non-limitative example of which is glucose), probes 10, buffers (non-limitative examples of which include Tris, HEPES, phosphate, and the like), mediators (non-limitative examples of which include ferricyanide, ferrocene derivatives, phenazine methosulfate (PMS), Ru(III) complexes, ubiquinone ($Q_0$), Os complexes, and the like), stabilizers (non-limitative examples of which include $CaCl_2$, $MgCl_2$, and the like), redox indicators (non-limitative examples of which include dichloroindolephenol (DCIP), resazurin, thionine, and the like), enzyme thermal stabilizers, barriers, oligo binders, and/or mixtures thereof.

As depicted in FIG. 2, the intact labeled oligonucleotide 10 includes the sequence 12 having a co-enzyme as the co-factor (CF) 14 conjugated thereto. During the DNA amplification process, 5'→3' exonuclease activity of DNA polymerase enzyme 19 results in the hydrolysis of the probe 10. The size and locations of DNA being amplified (amplicon) is determined, at least in part, by a pair of primer oligonucleotides (arbitrarily designated forward and reverse primers) which are complementary and hybridize specifically to double stranded template DNA. As depicted, forward primer 18 is not attached to the DNA polymerase enzyme 19. It is to be understood that the forward primer 18 in the PCR mix hybridizes to a complementary region on the target DNA 17. The DNA polymerase enzyme 19 has a binding site that recognizes this structure. In this case, the target DNA 17 which hybridizes to the primer 18 is a DNA double stranded structure that contains a 3' terminus. The DNA polymerase enzyme 19 then extends the primer 18 by filling in complimentary bases over the single stranded template.

The hydrolysis of the labeled nucleotide 10 releases (as depicted by the lightening bolt) a fragment 16 containing the co-factor (CF) 14. The co-factor (CF) 14 (e.g. a co-enzyme, prosthetic group, or metal-ion activator) of the fragment 16 may then combine with and activate an apo-enzyme 20 immobilized on the surface of a test strip 22 (a non-limitative example of which includes a PCR test strip). It is to be understood that the apo-enzyme 20 may also be present in solution when the assay is homogeneous. The combination of the fragment 16 and the apo-enzyme 20 forms a holo-enzyme 24, which is capable of catalyzing a reaction that converts a predetermined substrate 26 in the sample to a product 28 plus free electrons. These free electrons may reduce a mediator $M_{(R)}$, which is subsequently re-oxidized $M_{(Ox)}$ by a redox indicator (In(color)) (a non-limitative example of which includes a dye) that results in the color change of the redox indicator (In(color change)).

The activation of the apo-enzyme 20 by the fragment 16 and the subsequent reaction involving the holo-enzyme 24 results in the formation of an optically measurable enzymatic signal. It is to be understood that the optical measurement of the enzymatic signal corresponds to a measurement of the target DNA 17.

The embodiment shown in FIG. 2 is a homogeneous assay system. In such a homogeneous system, the intact labeled nucleotide 10 is substantially inactive. After the DNA amplification process, the PCR mixture solution (the labeled nucleotide 10, fragment 16, the multiplied target DNA 17) will be mixed with the mediator (M) and/or a co-substrate (i.e. a reactant that is transiently associated with the enzyme and becomes a product(s) that cooperates chemically with another substrate regarding formation of another product(s), a non-limitative example of which is an oxidant), the apo-enzyme 20, nucleic acids, redox indicators and any other desired ingredients/reagents for optical detection, such as those described herein. In such a homogeneous system, the intact labeled nucleotide 10 may desirably have the tendency not to bind with the apo-enzyme 20, not to activate the holo-enzyme 24, and to not generate an optical signal that is representative of the DNA sample 17.

Referring back to the DNA amplification processes, in an embodiment using an end-point detection DNA amplification process, holo-enzyme 24 activity (which generates the enzymatic signal) is measured before and after the entire process. The methods for detection include, but are not limited to visual color change, absorbance change, fluorometry, and the like. It is to be understood that a sample designation as to whether "positive (with target DNA)" or "negative (without target DNA)" for a given DNA sequence may depend, at least in part, on a predetermined criterion involving the magnitude of the change in optical signal observed before and after the amplification process. In one embodiment using end-point detection, the PCR and detection processes may be performed sequentially as two separate steps in two separate and/or different spatial environments. In another embodiment using end-point detection, the PCR and optical detection may be batch processed in one integrated step in the same spatial environment. In a non-limitative example using batch processing, thermophilic or thermally stabilized enzymes (non-limitative examples of which include sol-gel and probe encapsulated by biologically localized embedding (PEBBLE)) may be used.

In an embodiment using a real-time detection DNA amplification process, holo-enzyme 24 activity (which generates the enzymatic signal) is measured continuously, or in many closely spaced (in time) discrete measurements, throughout the entire process. The optical signal may be detected using the methods previously described under oxidative or reductive conditions. It is to be understood that a sample designation as to whether "positive (with target DNA)" or "negative (without target DNA)" for a given DNA sequence may depend, at least in part, on a predetermined criterion involving the magnitude of the Delta comparing signal measurements before and after the PCR for each thermal cycle. In one embodiment using real-time detection, the PCR and detection processes may be performed sequentially as two separate steps in two separate and/or different spatial environments. In another embodiment using real-time detection, the PCR and optical detection may be batch processed in one integrated step in the same spatial environment. In a non-limitative example using batch processing, thermophilic or thermally stabilized enzymes (non-limitative examples of which include sol-gel and PEBBLE) may be used.

Figure 3:
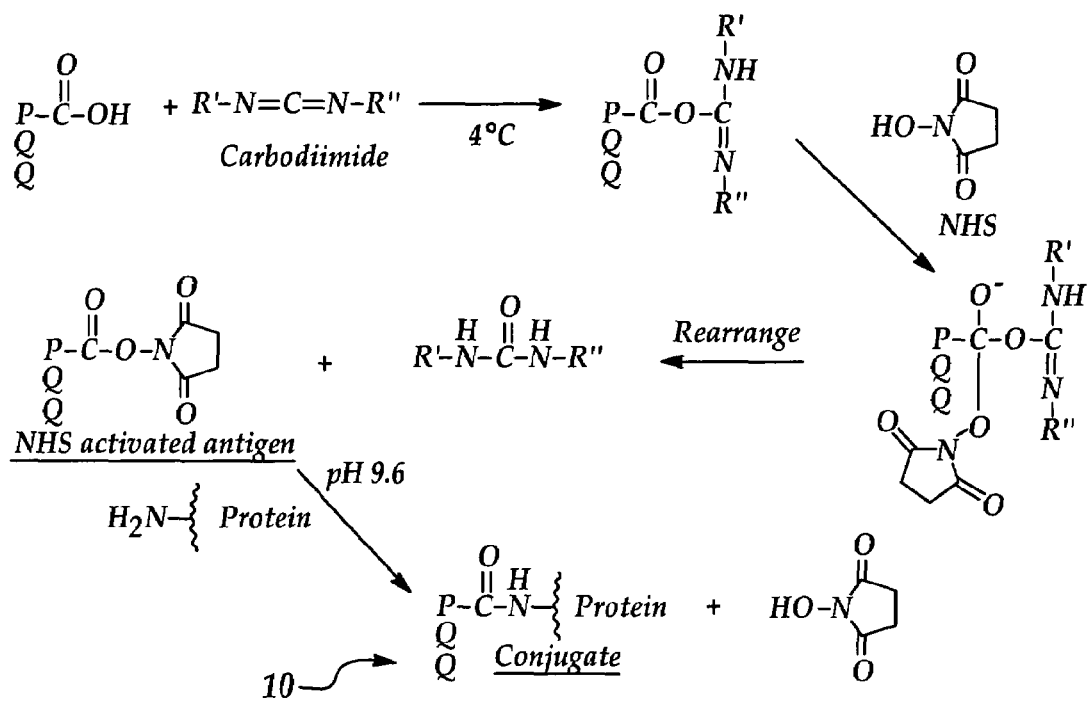
FIG. 3 is a schematic flow diagram illustrating an embodiment of making an embodiment of a prosthetic group (PQQ) labeled protein (protamine) or polypeptide.

Referring now to FIG. 3, an example embodiment of making a prosthetic group labeled protein (i.e. marker molecule) is schematically depicted. It is to be understood that the co-factor (CF) 14 (in this case PQQ) may be conjugated at any spot along the primary amine site in the protein sequence.

In the non-limitative example shown in FIG. 3, the co-factor (CF) 14 (PQQ) is conjugated to the primary amine site at the end of the protein (a non-limitative example of which includes protamine) by adding 1-(3-dimethylaminopropyl)-3-ethylcarbodiimide (EDC or EDAC; 1 mg/ml) into a PQQ solution. After reacting the PQQ with EDAC at about 4° C., N-hydroxysuccinimide (NHS; 0.6 mg/ml) is injected into the solution and shaken. This results in the modification of the carboxyl groups and the formation of amine-reactive NHS esters. A solution of the desired protein may be added to the activated PQQ and allowed to react. The non-limitative example PQQ-protamine conjugate (marker molecule 10) shown in FIG. 3 is capable of monitoring peptide cleaving enzyme (e.g., trypsin) activity.

Figure 4:
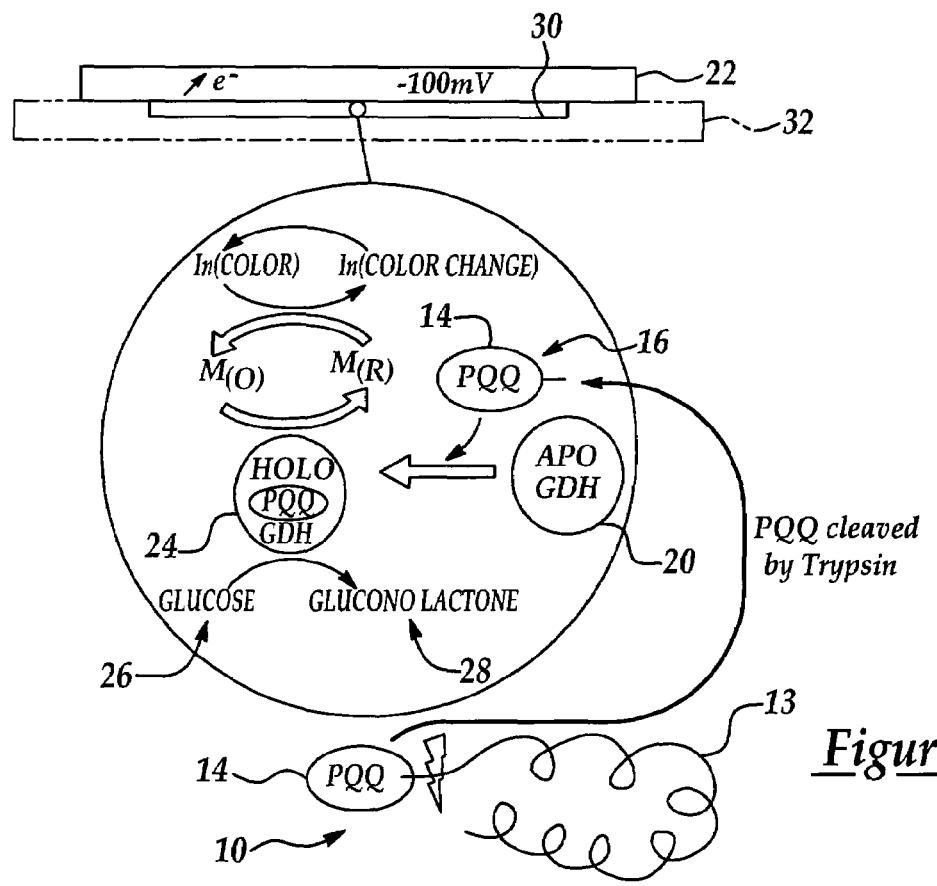
FIG. 4 is an exploded, partially schematic view of a specific example embodiment of a method of monitoring peptide cleaving enzyme activity.

Referring now to FIG. 4, an embodiment of the method of monitoring peptide cleaving enzyme (e.g., trypsin) activity in a sample using an embodiment of the marker molecule 10 is schematically depicted. Embodiment(s) of the method integrate cleaving processes with enzymatic signal amplification. More specifically, peptide cleaving enzyme (e.g., trypsin) activity may trigger enzymatic generation or amplification of a measurable optical enzymatic signal. The enzymatic signal(s) may be optically detectable via absorbance change, fluorescence, visual color change, and combinations thereof.

Embodiment(s) of the method generally include exposing an embodiment of the co-factor labeled protein, peptide, or oligonucleotide 10 to cleaving activity (e.g. peptide, protein, or nucleotide cleaving activity), combining a co-factor (CF) 14 fragment 16 to an apo-enzyme 20, and optically detecting an enzymatic signal that results from the combination of the fragment 16 with an apo-enzyme 20. It is to be understood that these steps may be performed substantially simultaneously or sequentially.

Cleaving enzyme activity processes may include formulating a sample such that it is compatible with desired chemistries for enzymatic signal amplification and optical detection. Such a formulation may include, but is not limited to the following: substrate(s) (a non-limitative example of which is glucose), marker molecules 10 (e.g. PQQ-protamine conjugate(s)), buffers (non-limitative examples of which include Tris, HEPES, phosphate, and the like), mediators (non-limitative examples of which include ferricyanide, ferrocene derivatives, phenazine methosulfate (PMS), Ru(III) complexes, ubiquinone ($Q_o$), Os complexes, and the like), stabilizers (non-limitative examples of which include $CaCl_2$, $MgCl_2$, and the like), redox inhibitors (dichloroindolephenol (DCIP), resazurin, thionine, and the like), enzyme thermal stabilizers, barriers, oligo binders, and/or mixtures thereof.

As depicted in FIG. 4, the intact marker molecule 10 includes the protein (e.g., protamine) 13 having PQQ as the co-factor (CF) 14 conjugated thereto. Cleaving enzyme (e.g., trypsin) activity results in the hydrolysis of the marker molecule 10. The embodiment depicted in FIG. 4, and in particular the exploded portion, is an assay system in which the test strip 22 is coated with a film 30 including the mediator (or co-substrate), the indicator, and the apo-enzyme 20 (e.g. apo-GDH), which is physically separated from the solution containing the marker molecule 10 via an optional film 32.

The hydrolysis of the marker molecule 10 by peptide cleaving enzyme (e.g., trypsin) releases (as depicted by the lightening bolt) a fragment 16 containing the co-factor (CF) 14. The fragment 16 containing the co-factor (CF) 14 may then combine with and activate an apo-enzyme 20 immobilized on the surface of a test strip 22 or a working electrode. It is to be understood that the apo-enzyme 20 may also be present in solution when the assay is homogeneous. The combination of the fragment 16 and the apo-enzyme 20 forms a holo-enzyme 24, which is capable of catalyzing a reaction that converts a predetermined substrate 26 in the sample to a product 28 plus free electrons. These free electrons may reduce a mediator $M_{(R)}$, which is subsequently re-oxidized $M_{(Ox)}$ by a redox indicator (In(color)) (a non-limitative example of which includes a dye) that results in the color change of the redox indicator (In(color change)).

The activation of the apo-enzyme 20 by the fragment 16 and the subsequent reaction involving the holo-enzyme 24 results in the formation of an optically measurable enzymatic signal. It is to be understood that the optical measurement of the enzymatic signal corresponds to monitoring cleaving enzyme activity.

The embodiment shown in FIG. 4 is a homogeneous assay system. In such a homogeneous system, the intact marker molecule 10 is substantially inactive. After or during the cleaving process, the mixture solution (the PQQ-protamine conjugate 10 and fragment 16) will be mixed with the mediator (M) and/or a co-substrate (i.e. a reactant that is transiently associated with the enzyme and becomes a product(s) that cooperates chemically with another substrate regarding formation of another product(s), a non-limitative example of which is an oxidant), the apo-enzyme 20, redox indicators and any other desired ingredients/reagents for optical detection, such as those described herein. In such a homogeneous system, the intact marker molecule 10 may desirably have the tendency not to bind with the apo-enzyme 20, not to activate the holo-enzyme 24, and to not generate an optical signal that is representative of the cleaving enzyme.

Referring back to the cleaving processes, holo-enzyme 24 activity (which generates the enzymatic signal) is measured through the entire process in real time. The methods for detection include, but are not limited to visual color change, absorbance change, fluorometry, electrochemistry (potentiometry, amperometry, voltametry, etc.), and the like. In a non-limitative example using batch processing, thermophilic or thermally stabilized enzymes (non-limitative examples of which include sol-gel and probe encapsulated by biologically localized embedding (PEBBLE)) may be used.

Experimental

Figure 5:
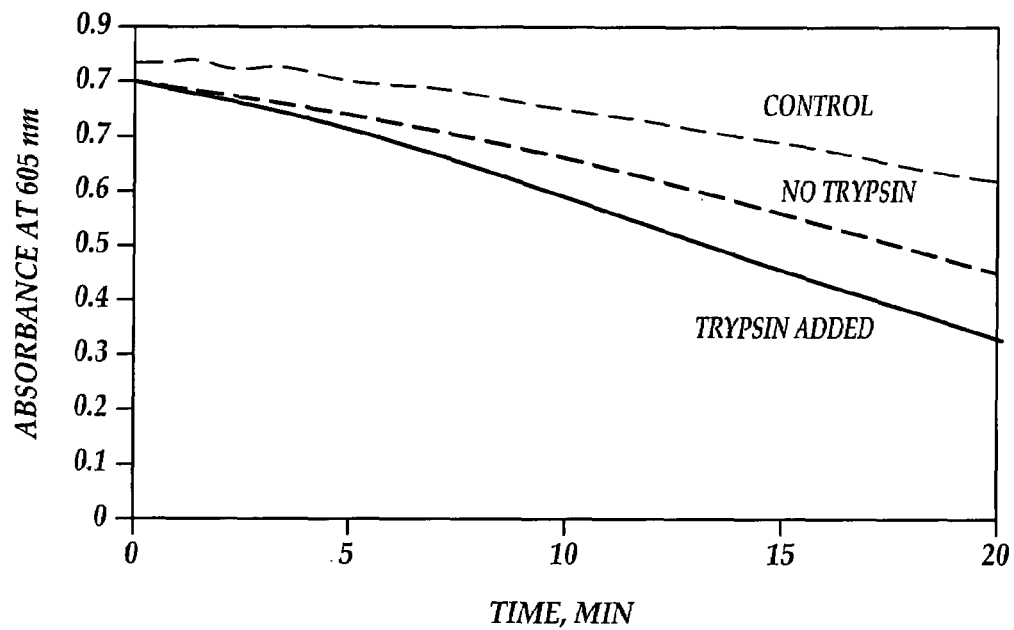
FIG. 5 is a graph depicting real time trypsin enzyme activity for cleaving protamine labeled with PQQ using DCIP as the redox indicator.
Figure 6:
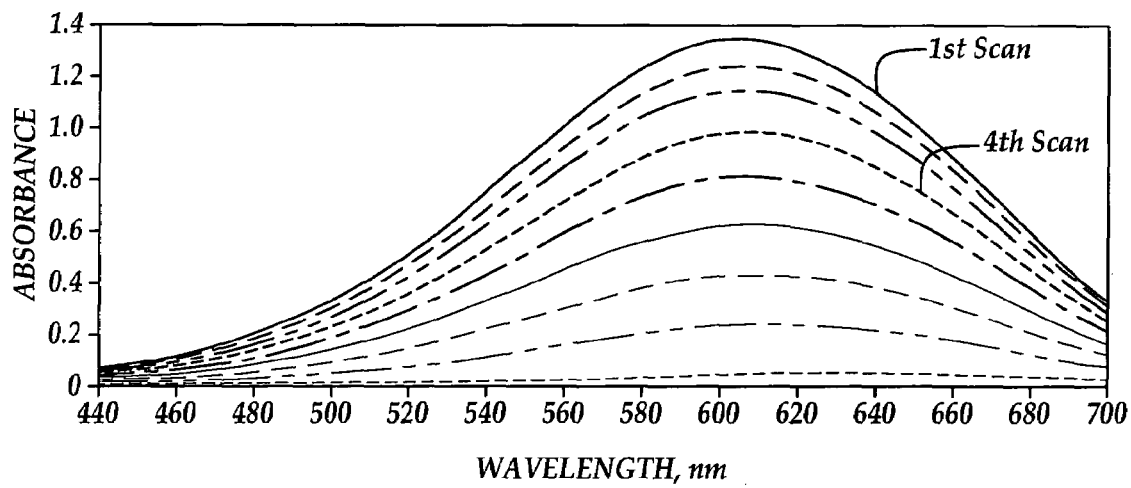
FIG. 6 is a graph depicting absorbance change of DCIP with time at 100 pM PQQ using enzymatic amplification.
Figure 7:
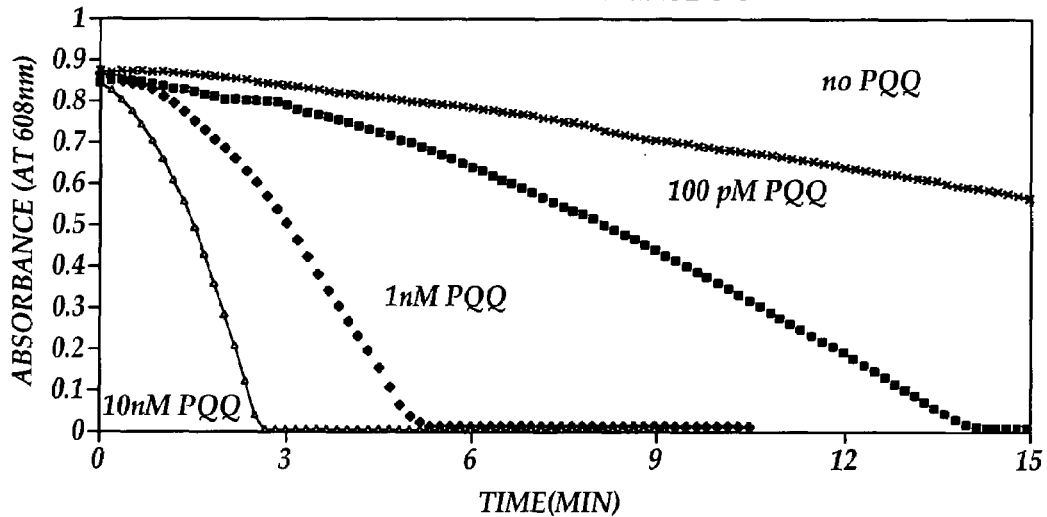
FIG. 7 is a graph depicting GDH enzyme activity for various concentrations of PQQ using DCIP as the redox indicator.
Figure 8:
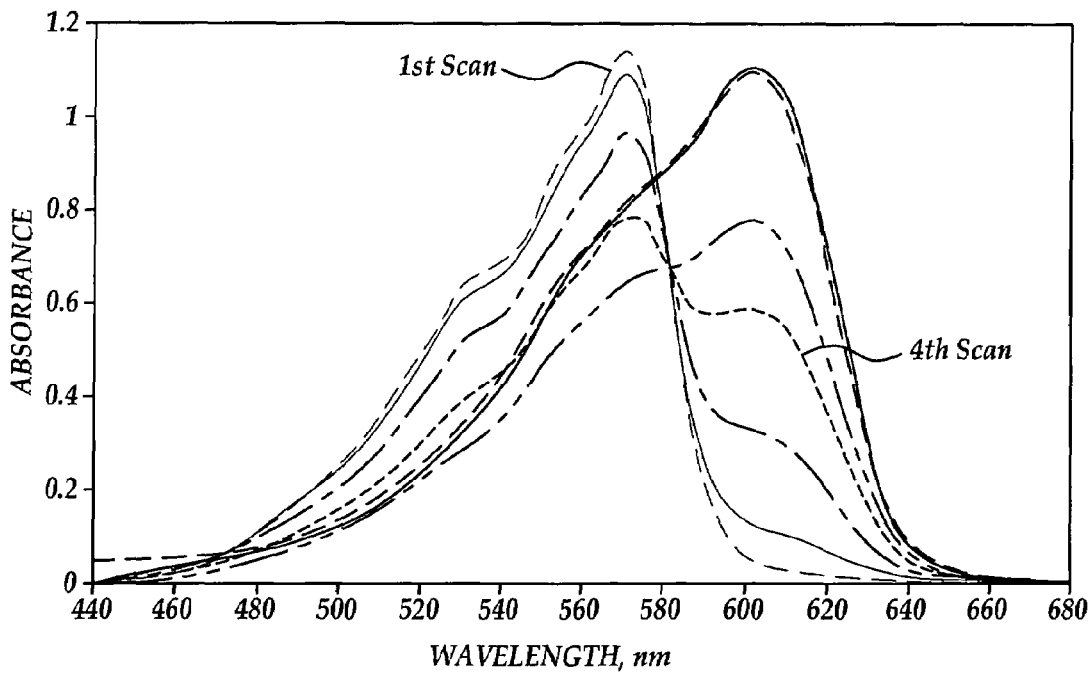
FIG. 8 is a graph depicting absorbance change of resazurin with time at 10 nM PQQ using enzymatic amplification.
Figure 9:
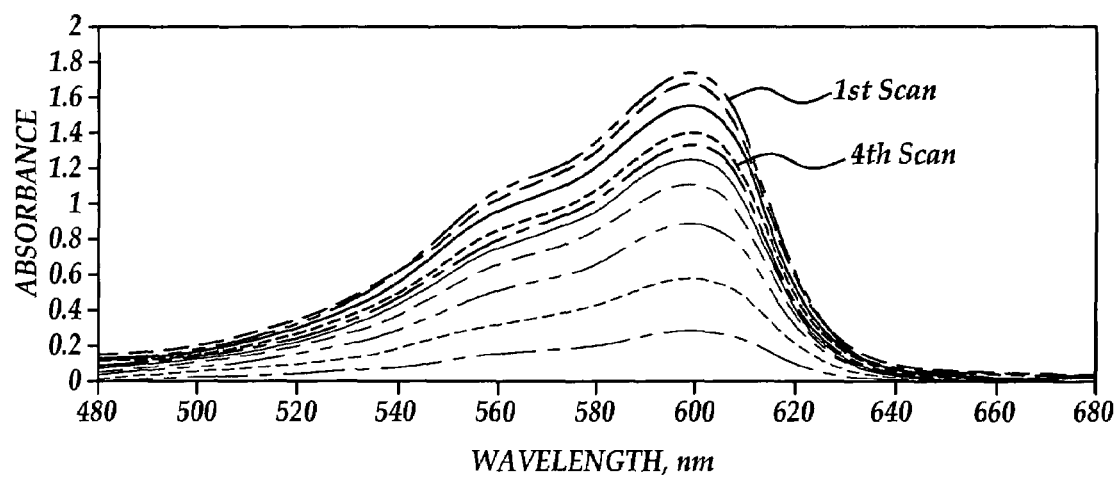
FIG. 9 is a graph depicting absorbance change of thionine with time at 10 nM PQQ using enzymatic amplification.

Homogeneous Optical Assay for Trypsin Activity with GDH and PQQ-Protamine Marker Molecule The PQQ-protamine marker molecule (4 nM) solutions included APO-GDH (1 μM), 0.2 mM $CaCl_2$, and 40 mM Glucose. 60 μM PMS and a redox indicator (0.3 mM DCIP) were also added. (See FIG. 5)

Homogeneous Optical Assay for DNA with GDH and PQQ (See FIGS. 6-9)

The PQQ solutions (variable concentrations) included APO-GDH (1 μM), 2 mM $CaCl_2$, and 40 mM Glucose. 50 μM PMS and a redox indicator (0.1-0.2 mM DCIP, 0.025 mM resazurin, or 0.05 mM thionine) were also added. PQQ at 0.1 nM was detectable.

While several embodiments have been described in detail, it will be apparent to those skilled in the art that the disclosed embodiments may be modified. Therefore, the foregoing description is to be considered exemplary rather than limiting.

What is claimed is:

1. A method of detecting a target DNA in a sample, the method comprising:

performing a DNA amplification process on the sample, wherein the DNA amplification process uses an amplification mixture including at least an intact labeled oligonucleotide, a DNA polymerase enzyme, and the target DNA, wherein the target DNA is from phakopsora pachyrhizi;

exposing the intact labeled oligonucleotide in the amplification mixture to exonuclease activity of the DNA polymerase enzyme in the amplification mixture, the intact labeled oligonucleotide including a site-specific sequence and a co-factor conjugated to the site-specific sequence, thereby hydrolyzing the intact labeled oligonucleotide and releasing a fragment of the oligonucleotide including the co-factor, wherein the site specific sequence is 5'-amino-hexyl-CCAAAAGGTACACCT-GTTTGAGTCA-3' (SEQ ID NO: 1), and the co-factor is pyrroloquinoline quinone;

combining the fragment with an apo-enzyme, wherein combining the fragment including the co-factor with the apo-enzyme produces an enzymatic signal that is optically detectable; and optically detecting the enzymatic signal, thereby detecting the target DNA.

2. The method as defined in claim 1 wherein the DNA amplification process is at least one of real time PCR, end-point PCR, and RCA.

3. The method as defined in claim 2 wherein the DNA amplification process is real time PCR and wherein holoenzyme activity, which generates the enzymatic signal, is measured at predetermined intervals during the amplification process.

4. The method as defined in claim 2 wherein the DNA amplification process is end-point PCR and wherein holoenzyme activity, which generates the enzymatic signal, is measured prior to and after the amplification process.

5. The method as defined in claim 2 wherein the DNA amplification process includes exposing the sample to a PCR mixture including at least one of substrates, probes, buffers, mediators, stabilizers, redox indicators, and mixtures thereof.

6. The method as defined in claim 1 wherein the performing, exposing, combining, and detecting occur sequentially.

7. The method as defined in claim 1 wherein optically detecting the enzymatic signal may be accomplished via absorbance change, fluorescence, visual color change, and combinations thereof.

* * * * *